United States Patent [19]

Ung-Chhun et al.

[11] Patent Number: 5,795,483
[45] Date of Patent: Aug. 18, 1998

[54] METHOD OF SEPARATING LEUKOCYTES FROM BLOOD CELLS USING A LEUKODEPLETION FILTER

[75] Inventors: Neng S. Ung-Chhun, Lincolnshire; Richard J. Johnson, Mundelein, both of Ill.

[73] Assignee: Baxter International Inc., Deerfield, Ill.

[21] Appl. No.: 810,751

[22] Filed: Mar. 4, 1997

Related U.S. Application Data

[62] Division of Ser. No. 323,559, Oct. 17, 1994, Pat. No. 5,647,985.

[51] Int. Cl.[6] .................... B01D 37/00; B01D 39/02
[52] U.S. Cl. .................... 210/645; 210/503; 210/504; 210/505; 210/506; 210/508; 210/767; 422/101; 436/177; 436/178
[58] Field of Search .................... 210/645, 767, 210/503, 504, 506, 508, 505; 422/101; 436/177, 178; 427/501, 513; 428/365

[56] References Cited

U.S. PATENT DOCUMENTS

| | | | |
|---|---|---|---|
| 3,945,926 | 3/1976 | Kesting | 210/500.4 |
| 4,053,420 | 10/1977 | Marx | 210/435 |
| 4,130,642 | 12/1978 | Kikugawa et al. | 424/533 |
| 4,256,588 | 3/1981 | Hoehn et al. | 210/692 |
| 4,283,289 | 8/1981 | Meyst et al. | 210/448 |
| 4,330,410 | 5/1982 | Takenaka et al. | 210/767 |
| 4,358,476 | 11/1982 | Zimmer et al. | 427/494 |
| 4,399,035 | 8/1983 | Nohmi et al. | 210/500.2 |
| 4,416,777 | 11/1983 | Kuroda et al. | 210/446 |
| 4,596,657 | 6/1986 | Wisdom | 210/206 |
| 4,618,533 | 10/1986 | Steuck | 428/315.7 |
| 4,701,267 | 10/1987 | Watanabe et al. | 210/806 |
| 4,767,541 | 8/1988 | Wisdom | 210/749 |
| 4,810,378 | 3/1989 | Carmen et al. | 210/206 |
| 4,855,063 | 8/1989 | Carmen et al. | 210/249 |
| 4,880,548 | 11/1989 | Pall et al. | 210/767 |
| 4,915,848 | 4/1990 | Carmen et al. | 210/749 |
| 4,917,799 | 4/1990 | Masuda et al. | 210/435 |
| 4,919,823 | 4/1990 | Wisdom | 210/749 |
| 4,925,572 | 5/1990 | Pall | 210/767 |
| 4,936,993 | 6/1990 | Nomura | 210/446 |
| 4,936,998 | 6/1990 | Nishimura et al. | 210/496 |
| 4,943,287 | 7/1990 | Carmen | 604/408 |
| 4,976,861 | 12/1990 | Pall | 210/508 |
| 4,985,153 | 1/1991 | Kuroda et al. | 210/496 |
| 4,997,577 | 3/1991 | Stewart | 210/767 |
| 5,089,146 | 2/1992 | Carmen et al. | 210/206 |
| 5,092,996 | 3/1992 | Spielberg | 210/435 |
| 5,100,551 | 3/1992 | Pall et al. | 210/486 |
| 5,100,564 | 3/1992 | Pall et al. | 210/496 |
| 5,104,788 | 4/1992 | Carmen et al. | 210/516 |
| 5,128,048 | 7/1992 | Stewart et al. | 210/206 |
| 5,190,657 | 3/1993 | Heagle et al. | 210/490 |
| 5,229,012 | 7/1993 | Pall et al. | 210/767 |
| 5,252,222 | 10/1993 | Matkovich et al. | 210/436 |
| 5,258,126 | 11/1993 | Pall et al. | 210/767 |
| 5,258,127 | 11/1993 | Gsell et al. | 210/767 |

FOREIGN PATENT DOCUMENTS

| | | |
|---|---|---|
| 58983/90 | 1/1991 | Australia . |
| 0 370 584 | 5/1990 | European Pat. Off. . |
| 0 397 403 | 11/1990 | European Pat. Off. . |
| 0 406 485 | 1/1991 | European Pat. Off. . |
| 0 408 462 | 1/1991 | European Pat. Off. . |
| 0 419 346 | 3/1991 | European Pat. Off. . |
| 0 500 472 | 8/1992 | European Pat. Off. . |
| 0 561 379 | 9/1993 | European Pat. Off. . |

(List continued on next page.)

*Primary Examiner*—John Kim
*Attorney, Agent, or Firm*—Robert M. Barrett; Denise M. Serewicz; Bradford R. L. Price

[57] ABSTRACT

Novel blood cell fractionation means utilizes conventional filters coated with high molecular weight polyethylene oxide derivatives crosslinked to prevent leaching from filter surfaces. These fractionation means have a special efficacy in binding white blood cells from whole blood while simultaneously allowing red cells and platelets to pass in the effluent phase.

1 Claim, 2 Drawing Sheets

FOREIGN PATENT DOCUMENTS

| | | |
|---|---|---|
| 03000074 | 12/1988 | Japan . |
| 05034337 | 7/1991 | Japan . |
| 05087808 | 9/1991 | Japan . |
| 05148150 | 11/1991 | Japan . |
| 05148151 | 11/1991 | Japan . |
| 4-187206 | 7/1992 | Japan . |
| 5-194243 | 3/1993 | Japan . |
| 9303740 | 3/1993 | WIPO . |
| 9308904 | 5/1993 | WIPO . |

Sigma PEO Compound :

$$OCH_2CHCH_2O(CH_2CH_2O)_nCH_2CH_2O\text{-}R$$
with O-R substituent

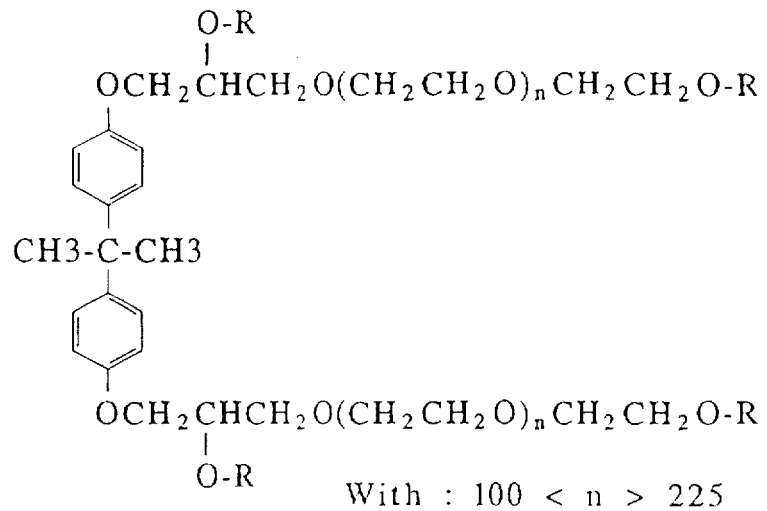

$$OCH_2CHCH_2O(CH_2CH_2O)_nCH_2CH_2O\text{-}R$$
$$|$$
$$O\text{-}R$$

With : 100 < n > 225

PEO : R = H

Imidazole-PEO : R = -CO-N

Tetraamino PEO : R = -CONH$(CH_2)_2NH_2$

Tetraacrylate PEO : R = -CH = $CH_2$

Shearwater PEO Derivatives :

1. $CH_3O(CH_2CH_2O)_nCH_2CH_2$-$R$

2. $ROCH_2CH_2O(CH_2CH_2O)_nCH_2CH_2O$-$R$

PEO : R = H

Imidazole-PEO : R = -CO-N

With : 250 < n > 450

3. 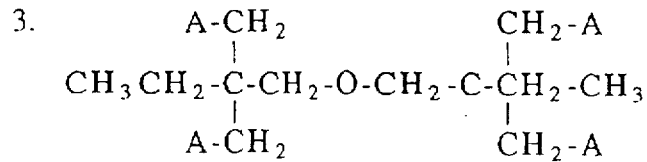

Tetraacrylate PEO 14 K daltons :

A = $CH_2$ = CH-COO-$CH_2CH_2O(CH_2CH2O)_{77}$

*FIG. 1*

METHOD OF SEPARATING LEUKOCYTES FROM BLOOD CELLS USING A LEUKODEPLETION FILTER

This is a divisional of U.S. patent application Ser. No. 08/323,559, filed on Oct. 17, 1994, U.S. Pat. No. 5,647,985.

BACKGROUND OF THE INVENTION

In processing whole blood for therapeutic administration to patients, it is desirable to separate the various cellular components. In particular, it is desirable to remove leukocytes because of their role in mediating immunologic reactions which can cause adverse clinical events such as allosensitization. For a review of adverse clinical sequellae to transfusion, see Sekiguchi, et al., Leucocyte-depleted blood products and their clinical usefulness, Ch. 5, pg. 26–33, from *The Role of Leucocyte Depletion in Blood Transfusion Practice* (1988). Furthermore, leukocytes are unessential for therapeutic supplementation of cell deficiencies in patients involving platelets and red cells. Thus, filter systems have been devised for passaging blood cells in order to remove leukocytes while allowing platelets or red blood to pass through for subsequent recovery.

There have been a number of approaches reported for leukocyte depletion. U.S. Pat. No. 4,330,410 discloses a packed fiber mass with leukodepletion properties comprising fibers of cellulose acetate, acrylonitrile, polyamide, or polyester. U.S. Pat. No. 4,925,572 discloses use of a gelatin coating to inhibit red blood cell (RBC) and platelet adhesion. Leukodepletion is accomplished primarily through physical entrainment of the cells in the fiber body, and adhesion of RBCs and platelets results from the gelatin coating. U.S. Pat. No. 4,936,998 discloses a strategy for leukodepletion in which a hydrophilic monomer containing hydroxyl or amido groups and functional nitrogen-containing groups such as primary or secondary amino groups is coated onto a filter matrix of known fibers such as polyester, polyamide, etc.

Modification of fiber surfaces has also been used to obtain materials with improved cell separation properties. For example, U.S. Pat. No. 4,130,642 discloses a packed column in which the packing material comprises an Egyptian cotton which has been de-fatted and bleached so that RBC readily pass through the column.

Some separation strategies involve multiple steps. U.S. Pat. No. 4,925,572 discloses a multistep method comprising an upstream porous element for removal of gels, a second element of finer porosity for removal of aggregated matter, and a final filtration step involving common fibers to which surface tension-reducing and improved wetting are obtained by radiation grafting of biocompatible moieties. Further description of leukodepletion methods is contained in Rikumaru, et al., Advanced methods for leucocyte removal by blood filtration, Ch. 6, pgs. 35–40, from *The Role of Leucocyte Depletion in Blood Transfusion Practice* (1988).

It is of utmost importance in designing leukodepletion strategies in which one goal is to obtain good recoveries of platelets and RBCs, to achieve separations without activating platelets or complement. It is also important that any coatings utilized to enhance the separations not be leached into solution, since the recovered cells are intended for intravascular administration to patients. One approach embodies a filter composed of a porous polymer material with continuous pore structure having a coating combining a nitrogen-containing functional group with a polyethylene oxide chain having 2–15 repeating units (See Jap. Kokai Patent Application No. Hei 5 [1993]-194243). This material is said to entrap leukocytes while giving high yields of platelets.

The use of polyalkylene oxide polymers is well-known in the construction of biocompatible materials, because of its low biological activity in activating cellular and humoral components of blood, and in stimulating immune responses. However, the inertness of the polyalkylene oxide polymers may also interfere with the degree of separation that can be obtained with cell separation filters, unless combined with functional groups that enhance separation parameters. A suitable combination of coating components has not heretofore been developed which is efficacious for cell separations from whole blood as distinct from semi-purified cell suspension mixtures.

SUMMARY OF THE INVENTION

Most blood available as a source for cell separation is whole, and not pre-fractionated. It generally is packaged in one unit (approximately 350–450 ml) plastic bags and is citrated to prevent clotting. Once blood becomes outdated for use in fresh transfusions, it may be fractionated. It would be highly desirable to be able to leukodeplete and separate platelets and RBC from such blood stores directly and immediately rather than wait until it is partially fractionated.

Accordingly, it is an object of the present invention to provide blood cell fractionation means for removing leukocytes from whole blood while permitting recovery in high yield of platelets and red blood cells. It is a further object of the present invention to obtain efficacious cell fractionation through a filter without leaching of coating materials which facilitate the differential separation. It is a further object to be able to coat filters and other cell fractionation means so that permanency is attained without covalent interaction with the filter matrix itself, requiring particular functional groups which may interfere with or defeat the object of differential cell separation.

Summarizing briefly, the present invention provides blood cell fractionation means comprising a filter matrix, preferably having a fibrous structure, which is coated with a chemical condensation product, prepared by reaction insitu of a first electrophilically active, high molecular weight polyalkylene oxide, and a second high molecular weight polyalkylene oxide derivative, which is either a tetraaminopolyalkylene oxide or a bifunctional dihydroxy- or diamino- polyoxyalkylene derivative, or combination thereof. Alternatively, in another embodiment, the coating may be an isopolymer of a high molecular weight tetraacrylatepolyalkylene oxide, polymerized by exposure to radiation.

The condensation reaction occurs insitu, i.e. after one polymer is dried onto the fibrous fractionation matrix, the second polymer is then contacted with the matrix, and the condensation reaction occurs spontaneously at a temperature between 5 degrees and about 200 degrees centigrade. The electrophilically active, high molecular weight polyalkylene oxide compound has the general structure Y-PEO-R-PEO-Y wherein Y is a reactive moiety selected from an oxycarbonylimidazole, tresyl-, tosyl-, N-hydroxysuccinimidyl, and p-nitrophenyl-activated esters; acrylates; glycidyl ethers; and aldehydes. The oxycarbonylimidazole leaving group is preferred, as will be apparent from the detailed specification. R is a spacer molecule (a chemical backbone) consisting of either bisphenol A (4,4'-(1-methylethylidene)bisphenol) or bisphenol B (4,4'-(1-methylpropylidene)bisphenol), and PEO stands for polyalkylene oxide.

In the method of preparing the cell fractionation means of the present invention, a first polymer comprising an electrophilically active, high molecular weight polyalkylene oxide compound, having terminal leaving groups as indicated herein above, oxycarbonylimidazole being preferred, is applied to the surface of the cell fractionation means matrix, then drying the first polymer onto the matrix, followed by applying a second polymer consisting of either a tetraamino-, a diamino-, or a dihydroxy- polyalkylene oxide, or combination thereof. The reaction between the polymers occurs spontaneously, and an incubation at a temperature from about 5 degrees to about 200 degrees Centigrade is continued for a time sufficient to obtain substantial completion of crosslinking.

In carrying out cell separations according to the present invention, a specimen containing a mixture of blood cells either in the form of a blood fraction or subfraction, or whole blood itself is contacted with cell separation means consisting of a fibrous structure, having a coating of chemical structure herein above defined, removing the cell separation means to which leukocytes have adhered, thereby separating leukocytes from the red blood cells and platelets. In a preferred embodiment, the cell separation means is a filter, through which the blood or other cell mixture is passed, with the result of removing leukocytes without substantial loss of platelets and red blood cells. In this way a transfusible unfractionated blood can be prepared which is fully functional upon administration, but with a greatly reduced risk of adverse immunologic events.

BRIEF DESCRIPTION OF THE DRAWINGS

FIG. 1 is a schematic of the chemical structure of the polymers of the preferred embodiment.

DETAILED DESCRIPTION OF THE PREFERRED EMBODIMENT

Figure 3:
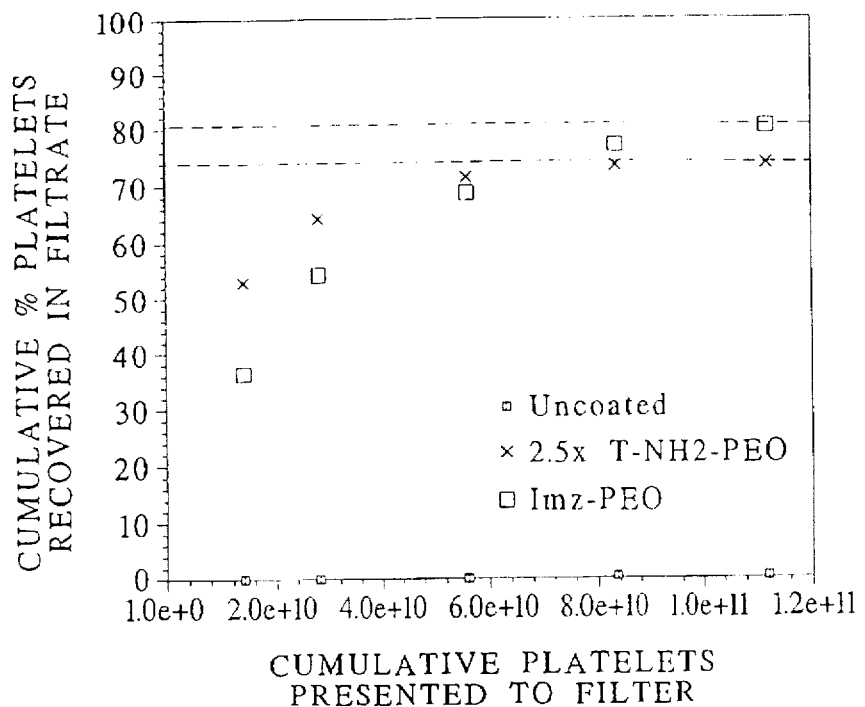
FIG. 3 illustrates the relative platelet recovery obtained with PEO-coated and uncoated Asahi R-2000 filters.

The present invention comprises blood cell fractionation means comprising a matrix having a fibrous structure, and the matrix further characterized in having a coating applied to it which changes its surface properties with respect to cellular adherence of blood cell containing fluid coming into contact therewith. In the preferred embodiment, the matrix is a packing material contained within a column, or a fibrous material compressed into a filter and held in a filter housing of conventional design and construction, although other configurations of a solid matrix contacting a fluid are within the scope of the invention.

Since the coating of polymers and the chemical reactions which are carried out to create a generally molecularly continuous polymeric surface on the matrix fibers do not require covalent or noncovalent interaction with any chemical moiety present on the native surface of the matrix, the coating itself is independent of the chemical and physical identity of the matrix. Thus, the coating is intended to be universally applicable to any filter available in the cell separation art. Examples include, without limitation, filters having a high glass content, as in glass fiber mats, filters with less or no glass content such as a filter comprising a mixture of glass and polyester, and a polyethylene terephthalate platelet filter coated with hydroxyethylmethyl-methacrylate.

Filter housings which may be conveniently used are manufactured conventionally. Examples of such housing are Swinney plastic manifolds manufactured by Gelman, pediatric Enterprise Housings, or Intermediate Enterprise Housings. The correct size correlations of filters to correspondingly suitable housings will be apparent to those skilled in the art.

The only limitation applicable to the blood cell fractionation means is a surface which is incompatible with the polymer solutions. Even in the instance where molecular wetting is not obtainable with the polymer solutions, techniques utilizing emulsifiers and phase penetrants may be useful in achieving adequate coating. To Applicants' knowledge, none of the blood cell fractionation filter materials currently available commercially are to be excluded from applicability to the present invention.

For manufacturing ease, chemical condensation reaction of the respective polymers is carried out insitu, i.e. a first free polymer is laid down on the matrix and dried, and then the second is contacted in solution with the matrix. The ensuing reaction then produces a skin-like sheet or layer of copolymerized material at the surface of the matrix. This reaction in the preferred embodiment proceeds spontaneously at temperatures generally in the range of 5 to 200 degrees centigrade. It is evident that the time for completion of the reaction will be slightly longer at cooler temperatures than for higher temperatures in accordance with kinetic thermodynamic principles. Generally, these reactions may be carried out at ambient temperatures, as disclosed in the Examples, but very little experimentation will be required by those skilled in the art to adjust the reaction times to a particular desired temperature of reaction.

The first polymer to be contacted with the filter (as by soaking to saturation) is a high molecular weight electrophilically active polyalkylene oxide. Electrophilically active means that a polyalkylene oxide polymer contains a oxycarbonyl moiety reactive with a nucleophilic center such as an amino or hydroxyl group contained in a second polymer. In a particularly preferred embodiment, a primary amine serving as a nucleophile, reacts with the carbonyl group of the imidazole-polyalkylene oxide polymer to form, upon reaction, an N-substituted carbamate bond where the carbonyl moiety from a cross-linker is incorporated into the new bond. These polymer entities must be high molecular weight, in the range of about 13,000 to 24,000 daltons, preferably about 20,000 daltons. Thus the preferred molecules shown in FIG. 1 for reaction on matrices will have n values of about 100–225. High molecular weight, as herein defined, is important because it was determined empirically that lower molecular weight materials tended to markedly reduce platelet recovery.

A first electrophilic polyalkylene oxide polymer will have a terminal leaving group reactive with an amine or hydroxyl containing second polyalkylene oxide. Suitable leaving groups on the first polymer for achieving acceptable chemical condensation are imidazoyl-, tresyl-, tosyl-, acryloyl-, and N-hydroxysuccinimidyl-. Additionally the structure of the electrophilic polymer can further be defined by the general expression: Y-PEO-R-PEO-Y, wherein Y is selected from the following group singly or in combination: oxycarbonylimidazole; trsyl-, tosyl-, N-hydroxysuccinimidyl-, and p-nitrophenyl-activated esters; acrylates; glycidyl ethers; and aldehydes, and R is a spacer defined as a backbone to which the two polyalkylene arms are attached, consisting preferably of bisphenol A or B. Bisphenol A is preferred, as shown in the structure of FIG. 1.

We have also determined that the imidazole derived polyalkylene oxides give the best results, perhaps because the reaction proceeds somewhat better, or perhaps because residual unreacted groups improve leukoadhesion. In any event, Applicants do not wish to be bound to any particular theory, but disclose the result as a guide to those experienced in the art. In general, polyalkylene means polyethylene or polypropylene, since these are the most common polyalkylene oxides used in biocompatibility applications. However, Applicants consider other polyalkylene oxides up to polybutylene oxide to be within the scope of the invention.

In a lesser embodiment, a tetra or diacrylate terminal derivative of polyalylene oxide may be isopolymerized by first contacting with the matrix, followed by irradiation with UV light or gamma rays to effect free radical polymerization. The resulting coated filter matrix is leukodepletive with adequate recoveries of platelets and red bloods cells, but is not a efficacious as the other embodiments of the invention set forth herein.

In the method of the present invention, insitu chemical condensation is carried out to mold the copolymer skin to the contours of the matrix fiber bed. It is important that the electrophilically active polyalkylene oxide by deposited on the matrix first, dried, and then further contacted with the second amino- or hydroxy- containing nucleophilic polymer. This teaching arises from empirical observation as to which method steps give best results in terms of platelet and RBC recovery, and leukodepletion, and the mechanistic or molecular basis for the observation is unknown to Applicants. In the drying step, drying in ambient air is adequate to "fix" the polymer in position, but light to moderate heat at various humidities down to less than 5% humidity or in vacuo may be applied to hasten the drying step in a manufacturing context.

The copolymerized material is highly stable to leaching, as shown in the Examples. In contrast to unreacted single polymer labeled with $^{125}I$ which is readily leached into filtrate, the fully copolymerized material made according to the method of the present invention is highly resistant to leaching, and is stable for preparation of therapeutically acceptable cell fractions.

In the method of separating cells according to the invention, a cell suspension or whole blood is filtered through the filter having the polymer coating as disclosed. The leukocytes adhere, and the platelets and RBCs pass through in the filtrate. More generalized methods of contacting the filter with a cell containing fluid are contemplated by this invention as well. For example, contacting by passaging through a packed column, or mixing cells in bulk with dispersed matrix in solution may be employed.

Other advantages of the present invention will be apparent from the Examples which follow.

EXAMPLE 1

Figure 2:
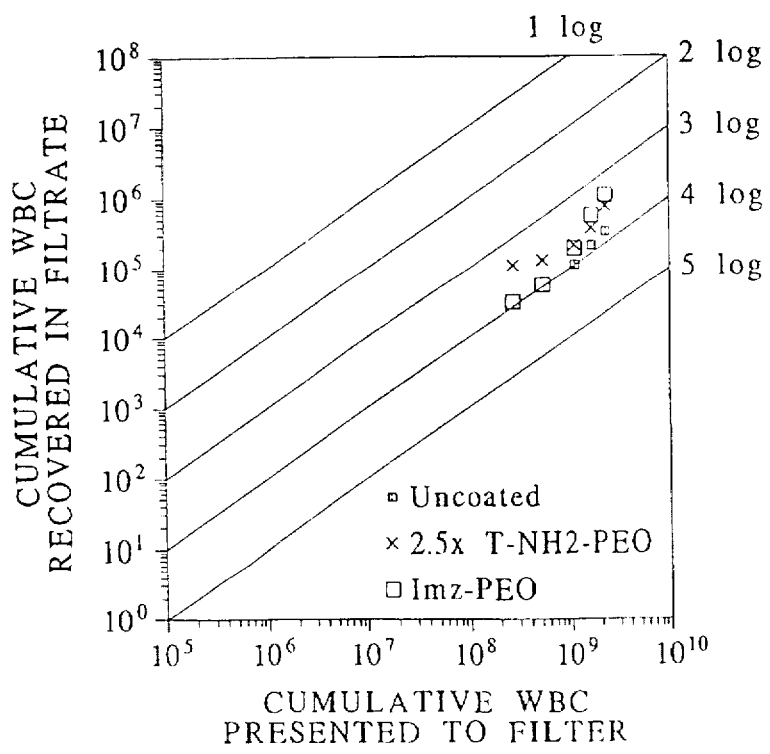
FIG. 2 illustrates the relative WBC depletion for PEO-coated and uncoated Asahi R-2000 filters. Log depletion is illustrated on the right side of the figure.

Oxycarbonyl imidazole-polyethylene oxide (Imz-PEO) with an average molecular weight of 20K daltons (Sigma Chemical Company), was first coated onto existing Asahi R-2000 filters by soaking the filter mats in a 2.5% solution of Imz-PEO. The mats were dried under vacuum. The amount of Imz-PEO bound to the mat was about 70 mg/gram of filter mat. Dried Imz-PEO-coated mats were cross-linked with bis[polyoxyethylene bis(amine)] (TAPEO, 20K daltons), obtained from Sigma Chemical Company. The cross-linking reaction was performed by soaking the Imz-PEO-coated mat in a water-methanol (1:1) solution of TAPEO at a 2.5 to 5.0 fold molar excess over the bound Imz-PEO. The reaction was allowed to proceed for at least 24 hours. The mats were dried again under vacuum. Dried cross-linked mats were washed extensively by soaking with water several times to remove any unbound PEO. After the final wash, the mats were dried again under a high vacuum. Cross-linked mats were stored at room temperature until used for blood filtration. In this example, the mats were used with pooled (ABO compatible), one day old, human whole blood, obtained from Interstate Blood Bank. The pooled whole blood was suspended about 3 feet above the filter unit, and the blood was allowed to flow by gravity through each of the different types of PEO-filter mats. An aliquot of whole blood (20 to 30 ml) was taken from the unit before filtration and was saved as a control (pre-sample). The filtered blood (post samples) and the pre-samples were counted for platelets with a Sysmex K-1000 cell counter and the WBC concentrations were determined by staining WBC nuclei (after lysing the sample) with propidium iodide and analyzing the stained samples with a FacScan flow cytometer. The results of WBC depletion and platelet recovery are illustrated in FIGS. 2 and 3 respectively. The degree of platelet recovery ranged from 75 to 80% with Imz-PEO-coated mats vs 0.5% for the uncoated mats. The amount of WEC depletion remained unchanged, in the range of 3 to 4 logs for all of the mats (Table 1).

TABLE 1

Filtration of Whole Blood Through PEO-Coated And Uncoated Asahi R-2000 Filter mats

| SAMPLE | WBC Depletion Depletion (log) | PLATELET Recovery (% Pre) |
| --- | --- | --- |
| Imz-PEG (no cross-linking) | 3.25 | 80 |
| 2.5x Crosslinked (Mat #1) | 3.39 | 74 |
| 2.5x Crosslinked (Mat #1) | 3.75 | 74 |
| Uncoated | 3.73 | 0.5 |

EXAMPLE 2

In this experiment, variables such as the age of the blood and the storage temperature were evaluated. The same PEO coated Asahi R-2000 filter mats described above were used for these studies. Units of whole blood were obtained fresh in-house, and stored at room temperature until used (about 2 hours). One day old blood, stored at room temperature or 4 degrees centigrade, were also obtained from Interstate Blood Bank. Each unit was allowed to flow through each PEO-coated filter and the samples were analyzed as described above. The results, summarized in Table 2, suggest that despite the utilization of various units of whole blood stored under different conditions, the yield of platelets obtained from PEO-coated Asahi R-2000 filters is dramatically improved (68 to 83%) as compared to uncoated mats (2%).

TABLE 2

Filtration of Whole Blood Through PEO-Coated And Uncoated Asahi R-2000 Filters

| SAMPLE | WBC Depletion (log) | PLATELET Recovery (% Pre) |
| --- | --- | --- |
| PEO-Cross Linked-Mats: | | |
| Interstate-RT (1 day old) #1 | −2.63 | 83 |
| Interstate-RT (1 day old) #2 | −4.01 | 68 |
| Interstate-4° C. (1 day old) #3 | −3.22 | 80 |

TABLE 2-continued

Filtration of Whole Blood Through PEO-Coated And Uncoated Asahi R-2000 Filters

| SAMPLE | WBC Depletion (log) | PLATELET Recovery (% Pre) |
|---|---|---|
| In-house-RT (~2 hrs) #1 | −3.25 | 76 |
| Uncoated Mats: Interstate-RT (1 day old) #1 | −3.50 | 02 |

EXAMPLE 3

In this example, tetraacrylate PEO derivatives were obtained either from Shearwater Polymer Inc., or synthesized from PEO 20K daltons obtained from Sigma (FIG. 1). The acrylate-PEO derivatives were coated onto composite mats by the same procedure as described in example 1. The dried acrylate-PEO-coated mats were subjected to gamma irradiation at a low dosage (2 megarads) to facilitate cross-linking of the PEO coating. The dried, coated mats were cut into circles of about 1.50 inches, and 3 layers of mats were placed into a small pediatric-sized housing for whole blood evaluation. One day old pooled whole blood, obtained from Interstate Blood Bank was used. The final volume of blood used per housing was about 75 ml. The results of these experiments, summarized in Table 3, demonstrate the improvement in platelet recovery upon coating mats with the PEO derivatives. However, the improvement in platelet recovery seen with the acrylate PEO derivatives is not as good as was observed with the Imz-PEO coated mats.

TABLE 3

Filtration of Whole Blood Through Various crylate-PEO-coated And Uncoated Composite Filters

| SAMPLE | WBC Depletion (log) | PLATELET Recovery (% Pre) |
|---|---|---|
| Uncoated | −2.20 | 43 |
| Sigma-Tetra-Acrylate-20K | −1.62 | 69 |
| Shearwater-Tetra-ACR-14K | −2.04 | 56 |
| Sigma-Tetra-Acrylate-20K Irradiated | −1.64 | 65 |
| Shearwater-Tetra-ACR-14K Irradiated | −1.91 | 65 |

EXAMPLE 4

The stability of these PEO coatings was investigated using radioactively labeled $^{125}$I-Imz-PEO and $^{125}$I-Tetraamino-PEO. The presence of the bis phenol A units in the structure of Imz-PEO or Tetraamino-PEO derivatives permitted conventional labeling of these molecules using $^{125}$I and iodo beads (Pierce Chemical Co.). In the first set of experiments, the $^{125}$I-Imz-PEO was first coated onto the mats and was cross-linked with unlabeled Tetraamino-PEO. In the second set of experiments, unlabeled Imz-PEO was coated onto the mats and then cross-linked with $^{125}$I-Tetraamino-PEO. Each $^{125}$I-PEO-coated mat was evaluated in a swinney housing (using a filter about 1 cm in diameter) with fresh whole blood. Four fractions of blood filtrate (~1 ml each) were collected and counted for the presence of $^{125}$I-PEO derivatives with a gamma counter. Each $^{125}$I-PEO-coated filter mat was also counted for radioactivity, before and after filtration. The amount of labeled PEO recovered on the mats after whole blood filtration varied from 87% to 95%. In contrast, 35% of the labeled Imz-PEO was leached off filter mats where no crosslinking reaction was performed.

TABLE 4

Stability of PEO-Coated Asahi R-2000 Filter Mats Measured With $^{125}$I-Imz-PEO or $^{125}$I-Tetraamino-PEO

| SAMPLE With $^{125}$I-label | $^{125}$I-PEO Coated Mats Recovered After Filtration (% Pre Labeled Mat) |
|---|---|
| 125-Imz-PEO-Tetraamino-PEO | 95% |
| Imz-PEO-125I-Tetraamino-PEO | 87% |
| 125I-Imz-PEO (not cross-linked) | 65% |

EXAMPLE 5

Various pre and post blood samples from the above experiments were further evaluated for complement activation by measuring C3a and C5a (by RIA) and for platelet activation by determining the percentage of platelets positive for the activation marker CD62. PLS10A platelet filters (Asahi) were included in this analysis as a control for comparison. The results for C3a and C5a is summarized in Table 5.

TABLE 5

C3a and C5a Levels In Blood Exposed To PEO-Coated And Uncoated Asahi R-2000 and PLS-10A Filters

| | C3a (ng/ml) | | C5a (ng/ml) | |
|---|---|---|---|---|
| SAMPLE | Pre-samples | Post-samples | Pre-samples | Post-samples |
| Cross-linked | 952 | 1,276 | 20 | 54 |
| Cross-linked | 538 | 614 | 0 | 19 |
| Cross-linked | 857 | 1,047 | 17 | 13 |
| Cross-linked | 1,103 | 1,149 | 28 | 34 |
| Cross-linked | 610 | 619 | 15 | 15 |
| Uncoated | 319 | 248 | 29 | 19 |
| Uncoated | 686 | 716 | 15 | 11 |
| PLS-10A | 964 | 4,057 | 22 | 66 |
| PLS-10A | 839 | 2,169 | 33 | 34 |
| PLS-10A | 328 | 1,727 | 9 | 25 |
| PLS-10A | 437 | 2,572 | 4 | 26 |

High levels of C3a and C5a were found in blood samples obtained from Asahi platelet filter PLS-10A. Although these PLS-10A filters have not been used with whole blood, it appears that the PLS-10A produces at least a 2 to 4 fold increase in C3a and C5a levels as compared to the corresponding pre-samples. These levels of C3a and C5a are higher than the amount of C3a and C5a produced by the PEO-coated Asahi R-2000. These results suggest that PEO-coated Asahi R-2000 filters are more biocompatible than the PLS-10A commercial filter used for platelet concentrate.

The percent of platelets expressing the activation marker, CD62, is a sensitive measure of the extent of platelet activation. Samples of whole blood were analyzed (pre and post filtration) using a FacScan flow cytometer to determine the percentage of platelets positive for CD62. This analysis revealed (Table 6) that no elevation in the percentage of CD62 positive platelets occurred during filtration on any of the mats investigated.

TABLE 6

Platelet Activation In Whole Blood Samples Exposed To Various Filters

| SAMPLE | % CD62 in Pre-samples | % CD62 in Post-samples |
| --- | --- | --- |
| Uncoated | 5.45 | 5.88 |
| Cross-linked-PEO | 4.45 | 4.78 |
| Cross-linked-PEO | 5.20 | 5.24 |
| Not Cross-linked-PEO | 5.45 | 3.27 |
| Not Cross-linked-PEO | 4.05 | 2.11 |
| PLS-10A | 5.45 | 2.10 |

We claim:

1. A method of separating blood cells comprising contacting blood cells with cell separation means consisting essentially of a fibrous structure, and a coating thereon, said coating being a copolymer of an electrophilically active, high molecular weight polyalkylene oxide compound and a high molecular weight polyalkylene oxide derivative selected from the group consisting of tetraaminopolyalkylene oxide and a bifunctional dihydroxy- or diamino- polyalkylene oxide, removing said cell separation means, thereby separating leukocytes which adhere to said cell separation means from the red blood cells and platelets which do not adhere to said cell separation means.

* * * * *